(12) United States Patent
Xu et al.

(10) Patent No.: US 8,094,910 B2
(45) Date of Patent: Jan. 10, 2012

(54) METHOD OF RECONSTRUCTING AN IMAGE FUNCTION FROM RADON DATA

(75) Inventors: Yuan Xu, Eugene, OR (US); Oleg Tischenko, München (DE); Christoph Hoeschen, Hebertshausen (DE)

(73) Assignees: State of Oregon Acting by and through the State Board of Higher Education on Behalf of the University of Oregon, Eugene, OR (US); Helmholtz Zentrum München Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 644 days.

(21) Appl. No.: 12/282,877

(22) PCT Filed: Mar. 14, 2007

(86) PCT No.: PCT/EP2007/002257
§ 371 (c)(1),
(2), (4) Date: Jan. 29, 2009

(87) PCT Pub. No.: WO2007/104552
PCT Pub. Date: Sep. 20, 2007

(65) Prior Publication Data
US 2009/0297009 A1    Dec. 3, 2009

(30) Foreign Application Priority Data
Mar. 14, 2006    (EP) .................................... 06005195

(51) Int. Cl.
G06K 9/00    (2006.01)
A61B 6/00    (2006.01)

(52) U.S. Cl. ............................ 382/131; 382/280; 378/19

(58) Field of Classification Search .................. 382/100, 382/128, 129, 130, 131, 132, 133, 134, 154, 382/168, 173, 181, 184, 194, 232, 254, 274, 382/276, 285–289, 295, 305, 312, 280; 378/10, 378/21, 19, 4, 15
See application file for complete search history.

(56) References Cited

U.S. PATENT DOCUMENTS
4,315,157 A * 2/1982 Barnes ............................ 378/10
(Continued)

FOREIGN PATENT DOCUMENTS
EP    1677253 A1    7/2006
(Continued)

OTHER PUBLICATIONS

Bortfeld, et al., Fast and exact 2D image reconstruction by means of Chebyshev decomposition and backprojection, Physics in Medicine and Biology, 44:1105-1120 (1999).

(Continued)

*Primary Examiner* — Seyed Azarian
(74) *Attorney, Agent, or Firm* — Klarquist Sparkman LLP

(57) ABSTRACT

A method of reconstructing an image function on the basis of a plurality of projection profiles corresponding to a plurality of projection directions through a region of investigation, each projection profile including a series of value positions, wherein measured projection values corresponding to projection lines parallel to the respective projection direction are assigned to respective value positions and a plurality of remaining value positions are empty, comprises the steps of (a) assigning first interpolation values to the empty value positions for constructing a plurality of interpolation profiles on the basis of the projection profiles, wherein the first interpolation values are obtained from a first interpolation within a group of measured projection values having the same value position in different projection profiles, and (b) determining the image function by applying a predetermined reconstruction algorithm on the interpolation profiles.

17 Claims, 5 Drawing Sheets

U.S. PATENT DOCUMENTS

| | | | |
|---|---|---|---|
| 4,365,339 A | | 12/1982 | Pavkovich et al. |
| 5,293,312 A | | 3/1994 | Waggener |
| 5,323,007 A | | 6/1994 | Wernick et al. |
| 5,592,523 A | * | 1/1997 | Tuy et al. .................. 378/19 |
| 6,343,110 B1 | * | 1/2002 | Li ............................. 378/19 |
| 6,944,259 B2 | * | 9/2005 | Yang .......................... 378/15 |
| 2009/0245456 A1 | * | 10/2009 | Tischenko et al. ............ 378/4 |
| 2009/0297009 A1 | * | 12/2009 | Xu et al. .................... 382/131 |

FOREIGN PATENT DOCUMENTS

| | | |
|---|---|---|
| EP | 1677254 A1 | 7/2006 |
| WO | WO 2006/069708 A1 | 7/2006 |
| WO | WO 2006/069709 A1 | 7/2006 |

OTHER PUBLICATIONS

Hanson, et al. Local basis-function approach to computed tomography, Applied Optics USA 24:4028-4039 (1985).

Herman, Image Reconstruction from Projections, the Fundamentals of Computerized Tomography, Academic Press, 316 pages (1980).

Kalender, Computed Tomography: Fundamentals, System Technology, Image Quality, Applications, $2^{nd}$ Edition, Wiley, John & Sons, Inc., ISN: 3895782165, 306 pages (2006).

International Search Report and Written Opinion for International Application No. PCT/EP2007/002257 (mailed Jun. 27, 2007), 9 pages.

* cited by examiner

US 8,094,910 B2

METHOD OF RECONSTRUCTING AN IMAGE FUNCTION FROM RADON DATA

ACKNOWLEDGEMENT OF GOVERNMENT SUPPORT

This invention was made with government support under Grant No. DMS-0201669 awarded by the National Science Foundation. The government has certain rights in the invention.

CROSS REFERENCE TO RELATED APPLICATIONS

This is the U.S. National Stage of International Application No. PCT/EP2007/002257, filed Mar. 14, 2007, which was published in English under PCT Article 21(2), which in turn claims the benefit of EPC Application No. 06005195.0, filed Mar. 14, 2006. Both applications are incorporated herein by reference.

TECHNICAL FIELD

The present invention relates to a method of reconstructing an image function from Radon data comprising a plurality of projection functions measured corresponding to a plurality of predetermined projection directions. Furthermore, the present invention relates to a method for imaging a region of investigation on the basis of the above reconstructing method.

TECHNICAL BACKGROUND

The non-destructive investigation of samples is an important objective in various technical fields like material sciences, non-destructive testing, medical examinations, archaeology, construction technique, techniques concerning security matters etc. One approach for obtaining an image of a sample e.g. by computer tomography (CT) is based on an irradiation through a sample plane from different projection directions with X-rays, followed by the reconstruction of the sample plane on the basis of attenuation data measured at different directions. The entirety of the measured attenuation data can be described in terms of so-called Radon data in a Radon space.

Different reconstruction methods for Radon data are known today (see e.g. the textbooks "Computed Tomography-Fundamentals, System Technology, Image Quality, Applications" by W. A. Kalender (1$^{st}$ edition, ISBN 3-89578-081-2); "Image Reconstruction from Projections: The Fundamentals of Computerized Tomography" by G. T. Herman, Academic Press, 1980; and "Einführung in die Computertomographie" by Thorsten M. Buzug (Springer-Verlag, Berlin 2004)). The conventional reconstruction methods can be summarized as iterative reconstruction methods and filtered back-projection methods.

The iterative reconstruction is an approximation method based on a plurality of iteration steps. The essential disadvantage of the iterative reconstruction of higher resolution images is that the iteration leads to extremely long calculation times. The filtered back-projection method relies in principle on the Fourier-slice theorem describing a relationship between the Fourier transform of the Radon data and Fourier transformed image data. A general disadvantage of using the Fourier-slice theorem lies in the fact that an interpolation step in the reconstruction results in errors and artifacts which have a tendency to increase with increasing space frequency. This disadvantage can only be avoided by using detectors with high resolution. However, the application of these detectors is limited in terms of dose burden, costs and data processing time.

An improved method of reconstructing image functions from Radon data is described in EP 04031043.5 (unpublished on the filing date of the present patent specification). With this method of using orthogonal polynomial expansions on the disk (in the following: OPED algorithm), an image function representing the region of investigation is determined from Radon data as a sum of polynomials multiplied with values of projection profiles measured corresponding to a plurality of predetermined projection directions through the region of investigation. The projection profile for each projection direction is constructed with projection values (attenuation values) detected with selected groups of e.g. X-ray irradiation beam components being parallel to said projection direction. The irradiation is emitted by an X-ray source at different views (or: angular positions) relative to the region of investigation. With the OPED algorithm as described in EP 04031043.5, the number of protection directions as well as the number of projection values in each projection profile typically is equal to the number of views.

The OPED algorithm has essential advantages in particular in terms of computational time reduction and producing images with improved signal-to-noise ratio. Furthermore, the imaging resolution can be improved in particular by using an increased number of detector elements with correspondingly reduced size. However, the improvement of the imaging resolution can be limited by the number of views. As the number of views is restricted with a typical computer tomography device to about 1.000 per full circle, an increased number of detector elements exceeding this value does not automatically yield an increased number of complete projection profiles. If the number of views is smaller than the number of detector elements, predetermined projection lines parallel to a particular projection direction are not irradiated through the region of investigation so that corresponding parallel beam components are not provided and related projection values cannot be measured. As the result, the projection profiles are incomplete and the image cannot be reconstructed correctly. A corresponding disadvantage can occur with the above mentioned filtered back-projection method.

A particular disadvantage of the OPED algorithm can occur as an adjustment of the reconstructed area to the area of the object without changing the scanning geometry is not easily possible with the OPED algorithm. In particular, the OPED algorithm as described in EP 04031043.5 has a drawback if zooming into the object is necessary. An example is given by the imaging of a part of a human body, e.g. a leg in a CT device. Only a few beam components of a fan beam covering the whole gantry will hit the leg, so that the projection profiles will contain only a few measured values for image reconstruction. Many data outside the leg would be set to be zero and the full potential of the OPED algorithm would not be used. An unsharpness of the leg image could be avoided by changing the fan beam and detector geometry only.

Another algorithm for the reconstruction of two-dimensional images from projections is described by T. Bortfeld et al. in "Phys. Med. Biol.", vol. 44, 1999, p. 1105-1120. The images are reconstructed from measured projection profiles, which are provided by projection values corresponding to parallel equidistant projection lines. As angle positions of the fan beam components are not identical with angle positions of an irradiating source in practice, the projection profiles are obtained by a rebinning step including an interpolation. This means that in a sinogram to be used for reconstruction the most positions are empty and interpolation is used for all these positions between neighboured not directly used measured values. However, the above potential problems of the OPED algorithm cannot be solved with the reconstruction technique of T. Bortfeld et al.

The above disadvantages are associated not only with the conventional CT image reconstruction, but also with all other image reconstructions based on Radon data.

OBJECTIVE OF THE INVENTION

The objective of the invention is to provide an improved method of reconstructing image functions from Radon data, avoiding the drawbacks of the above reconstructing and imaging techniques and leading to an increased range of applications in non-destructive investigations. In particular, the objective of the invention is to provide a reconstructing method yielding image functions with improved imaging resolution even with a limited number of views for irradiating an object under investigation. A further aspect of the objective of the invention is to provide an improved imaging method avoiding the disadvantages of the above imaging methods based on the collection of Radon data. In particular, the imaging method should allow an irradiation of the object with a limited fan angle without a loss of resolution. According to a further particular aspect, the objective of the invention is to provide an imaging method which allows a zooming into the object.

The above objectives are achieved with methods comprising the features of patent claims 1 or 11. Advantageous embodiments and applications of the invention are defined in the dependent claims.

SUMMARY OF THE INVENTION

According to a first aspect, the present invention is based on the general technique of reconstructing an image function on the basis of a plurality of interpolated projection profiles (interpolation profiles) corresponding to a plurality of projection directions through a region of investigation. The interpolation profiles include a series of value positions occupied with measured projection values corresponding to irradiated projection lines parallel to the respective projection direction and interpolation values provided for non-irradiated projection lines. If the number of views is smaller than the number of detector elements, projection values which cannot be measured are obtained by an interpolation (so-called: first interpolation). Measured projection profiles including empty value positions are completed by the first interpolation. Advantageously, the number of views can be reduced e.g. for reducing the radiation dose during imaging and/or the size of detector elements can be reduced e.g. for increasing the imaging resolution.

In particular, the method of the invention comprises the steps of assigning the first interpolation values to the empty value positions for constructing a plurality of interpolation profiles on the basis of the measured projection profiles and determining the image function as a sum of polynomials multiplied with the values of the interpolation profiles. On the basis of the interpolation profiles, the image function is calculated using a predetermined reconstruction algorithm, e.g. the above OPED algorithm. In this case, the image function is determined on the basis of sums of orthogonal ridge polynomials. Accordingly, the advantages of the OPED algorithm, which are described in EP 04031043.5, can be completely obtained with the imaging method of the invention. Alternatively, the image function is calculated using the conventional iterative reconstruction or filtered back-projection methods.

According to the invention, the first interpolation values are obtained from the first interpolation comprising interpolation routines each of which being conducted within a group of measured projection values which belong to different projection profiles, i.e. which belong to different projection directions or to different views. The first interpolation comprises an approximation for filling empty value positions between measured projection values having equal value positions in adjacent projection profiles.

The term "region of investigation" (ROI) generally refers to an object to be imaged or a part thereof. Generally, the ROI can be described as a 2-dimensional entity. For reconstructing a 3-dimensional image of the object, a plurality of ROI's is imaged. The term "projection direction" generally refers to the linear course of at least one energy input beam or beam component through the ROI in 3-dimensional space. The projection direction can be defined by angles relative to a coordinate system used. The term "view" indicates a geometric arrangement (or: angular positions in fan beam geometry) of an energy input beam source, like e.g. an X-ray source, relative to the ROI for irradiating the ROI according to a particular projection direction.

The Radon data measured at the ROI comprise a set of projection functions, which have been determined corresponding to a plurality of predetermined projection directions running through the ROI. Each projection function comprises data, which are collected with a certain number, which might in theory be infinite large, of "projections" parallel to the current projection direction. These projections are characterized by integrating over one-dimensional lines. By measuring a sufficient number of these integrated "projections" and adding the interpolation values, an image function of the object can be reconstructed from the Radon data.

Due to the discrete data collection in practice, the projection functions are indicated here as projection profiles. Each "profile" comprises a series of value positions, which are occupied with measured values according to "projections" parallel to the current projection direction or with interpolation values. The number of value positions corresponds to the number of detector elements detecting beam components of the fan beam through the ROI. The measured values of the projection profiles generally are determined by the modification (in particular attenuation, e.g. by absorption or scattering) of an energy input beam travelling through the ROI along the respective projection direction.

According to a preferred embodiment of the invention, the interpolation profiles are subjected to a further interpolation (so-called: second interpolation). Depending on the particular application, the second interpolation is applied to the complete interpolation profiles or parts of the interpolation profiles corresponding to predetermined portions of the ROI. The second interpolation comprises an approximation for filling intermediate value positions between the value positions of the interpolation profiles. To this end, the second interpolation comprises a plurality of interpolation routines each of which being conducted within a group of measured projection values and first interpolations values which belong to one of the interpolation profiles. With the second interpolation, advantages for a flexible zooming into the ROI or parts thereof can be obtained.

Advantageously, there are no particular limits with regard to the type of applied interpolation procedure. Depending on the particular application, at least one of the first and second interpolation may comprise e.g. a linear interpolation, where interpolation values are calculated with a linear approximation between the adjacent profile values, or e.g. any polynomial approximation. If, according to a particular preferred embodiment of the invention, at least one of the first and second interpolations is a spline interpolation, advantages are obtained in terms of approximation quality yielding a high image quality. The first and possibly the second interpolation values can be obtained from a cubic spline interpolation. The cubic spline function (n=3) has particular advantages in terms of stability (avoiding oscillations in the approximating spline), improved smoothing and easy computing. Alternatively, interpolation values are obtained from a spline interpolation with a spline function of order n with n>3.

According to a further advantageous embodiment of the invention, at least one interpolation parameter is set (adjusted) before or during the image reconstruction. The term "interpolation parameter" refers to any characteristic or quantity of at least one of the first and second interpolation, like e.g. the order of an interpolation function or even the type of interpolation. The essential advantage of this embodiment is given by the fact, that the quality of image reconstruction can be optimized e.g. depending on the object or the portion of the ROI investigated. In particular, the at least one interpolation parameter can be adjusted in dependence on a predetermined geometric feature of the region of investigation. Accordingly, the first or second interpolation can be adapted to a particular feature to be found in the ROI.

According to a particular preferred embodiment of the invention, the step of constructing the interpolation profiles includes a rescaling of the interpolation profiles. The rescaling of the interpolation profiles comprises an adaptation of the geometric size of the ROI or part thereof to the unit disk, on which the OPED algorithm is applied. Accordingly, a zooming effect can be obtained without increasing the number of beam positions (number of views). The rescaling yields stretched interpolation profiles including the region of investigation so that the unit disk for applying the OPED algorithm is covered.

Advantageously, the reconstructing method of the invention can be applied for calculating the image function from Radon data not only from X-ray computer tomography (CT), but also from other techniques like e.g. ultrasound tomography, PET imaging, light tomography, Gamma-ray imaging, SPECT imaging, or neutron based transmission detection.

According to a second general aspect of the invention, an imaging method for imaging the ROI is provided, wherein at least one energy input beam is directed at predetermined irradiation directions through the region of investigation and projection profiles are determined corresponding to the irradiation directions. The image function representing the ROI is reconstructed by subjecting the projection profiles to the reconstructing method of the invention.

The imaging method of the invention can be applied with different types of energy input beams used for providing the Radon data. The term "energy input beam" used herein refers to all types of a physical quantity, which travels along a straight line (or an essentially straight line) through the ROI while the energy carried is changed due to an interaction with the ROI. In particular, the term "energy input beam" covers electromagnetic radiation or particle radiation. Preferably, the energy input beam comprises X-rays. If an X-ray source device is used as the energy beam source device, computer tomography devices provided with at least one interpolation circuit can be used for implementing the imaging method of the invention.

Preferably, the at least one energy input beam comprises at least one fan or cone beam including a plurality of fan or cone beam components. Each measured projection profile comprises projection values measured with fan beam components along parallel projection lines associated by the same projection direction but being contained in different sets of fan beams. Advantageously, the projection profiles can be constructed simply by selecting the associated projection values from the collected detector data. In the present specification, reference is made to fan beams with a plane fan-shaped radiation distribution. The invention can be implemented in an equivalent way with at least one energy input beam comprising at least one cone beam including a plurality of cone beam components.

If, according to a preferred embodiment of the invention, the irradiation directions are set with one single fan beam by using a movable radiation source, advantages in terms of applying the available irradiation techniques can be obtained. The irradiation directions can be adjusted subsequently by rotating the radiation source around the object.

Depending on the application of the imaging method, further procedural steps for providing the requested image information in an appropriate format may follow. Preferably, an approximation of the image function is represented as a visualized image, e.g. with at least one 2- or 3-dimensional picture or a corresponding video representation (motion picture). Alternatively, the image function can be subjected to further image processing, e.g. for automatically detecting predetermined features. Advantageously, prior art image processing methods can be applied on the image function determined according to the invention. The provision of the visualized image comprises the step of calculating visualizations of the object, e.g. by converting the values of the image function into grey values.

Preferred applications of the inventions are in the technical fields like material sciences, non-destructive imaging, non-destructive testing, medical examinations, archaeology, construction technique, and techniques concerning security matters. Accordingly, the imaged object comprises e.g. a biological organism or a part thereof, a fluid composition, a solid material, a work-piece, and/or an object to be investigated for security reasons.

Further independent subjects of the invention are a computer program residing on a computer-readable medium, with a program code for carrying out the reconstructing method of the invention and an apparatus comprising a computer-readable storage medium containing program instructions for carrying out the reconstructing method of the invention.

BRIEF DESCRIPTION OF THE DRAWINGS

Further details and advantages of the invention are described in the following with reference to the attached drawings, which show in.

EMBODIMENTS OF THE INVENTION

The invention is described in the following with reference to the preferred application in computer tomography. It is emphasized that the invention can be implemented in an analogous way with the application of other types of energy input beams (like e.g. neutrons or light, e.g. in the VIS or IR range). Furthermore, the following description of the preferred embodiments mainly refers to the principles of constructing interpolation profiles, including data collection and data processing. Details of the structure and operation of CT devices used for implementing the invention are not described as long as they are known from conventional CT devices.

Furthermore, the invention is described in the following with reference to the preferred application of the OPED algorithm. The description of the OPED algorithm for image construction as described in EP 04031043.5 is introduced into the present specification by reference. If the image function is calculated using the conventional iterative reconstruction or filtered back-projection methods, the irradiating scheme can be adapted to the requirements of these algorithms.

The embodiments of the invention are illustrated with reference to schematic, non-scaled drawings. The detailed features of irradiation geometry, e.g. the number, thickness and angular distances of irradiation beam components or the rotation speed of the X-ray source can be selected by the skilled person in dependence on the particular task of imaging.

1. Image Reconstruction According to the Invention

Figure 1:
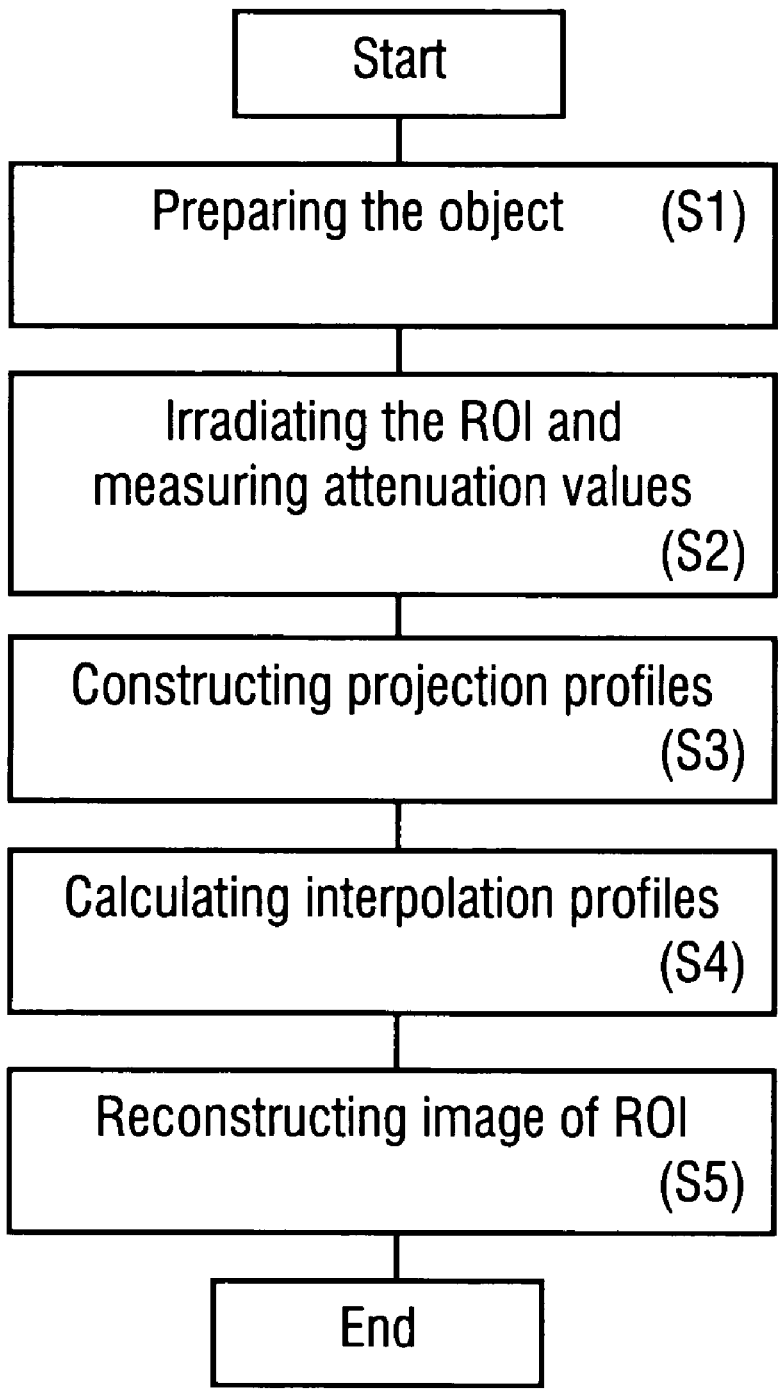
FIG. 1 a flow chart illustrating an embodiment of the imaging method according to the invention.

In FIG. 1, the steps for carrying out the imaging method of the invention are summarized. Firstly, the object to be investigated, like e.g. the head or another part of a patient's body is prepared (step S1). Preparing the object comprises a positioning of the object on a holding device in a CT device such that the region of investigation is aligned with a source-detector-unit of the CT device.

Subsequently, the object is subjected to the irradiation (step S2). An X-ray source is operated for generating a fan or cone X-ray beam directed towards the object and a detector device. The detector device comprises e.g. an array of flat panel detectors each with a plurality of detector elements, which are positioned with a fixed distribution around the gantry of the CT device. Alternatively, the detector device comprises e.g. one single flat panel detector with a plurality of detector elements. In this case, the detector device is rotated with the source-detector-unit around the gantry. Furthermore, step S2 includes measuring integrated attenuation values, wherein X-rays received with the detector device are detected.

Step S2 is continuously repeated for measuring projection values with a plurality of projection directions of irradiating the X-rays through the object. The projection directions are set e.g. by rotating the source-detector-unit around the gantry. Step S2 automatically includes a discretization of data. Due to the geometry of the detector device, discrete attenuation value data are recorded. During at least one of steps S1 an S2, the object can be further manipulated, e.g. by adding a contrast agent or by an intervention. This embodiment of the invention has particular advantages for a collection of dynamic images or imaging changing objects in particular in medical applications of the imaging method.

The projection values measured with the detector device are subjected to the steps of constructing the projection profiles (step S3), completing the projection profiles by constructing interpolation profiles (step S4) and data processing for reconstructing an image of the ROI (step S5). Step S4 can include a resealing of the calculated interpolation profiles. The diameter of the ROI is rescaled such that the interpolation profiles cover the unit disk used for applying the OPED algorithm. Each projection profile comprises a plurality of parallel projections, which are obtained by an assignment (or resorting) of the beam components measured with the detector device. With the assignment, the fan beam geometry becomes a parallel geometry as required for reconstructing an image from the Radon data, in particular with the OPED algorithm or the filtered back-projection method.

Figure 2:
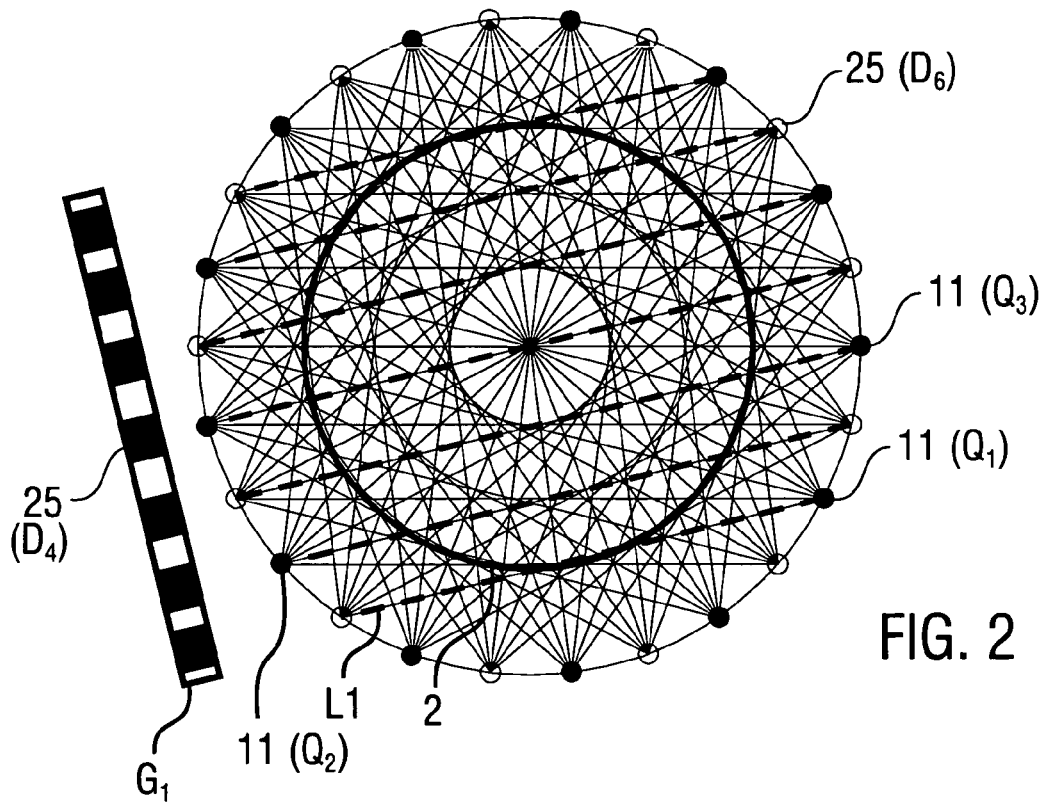
FIGS. 2 to 6 diagrams illustrating the principles of constructing interpolation profiles according to the invention.
Figure 3:
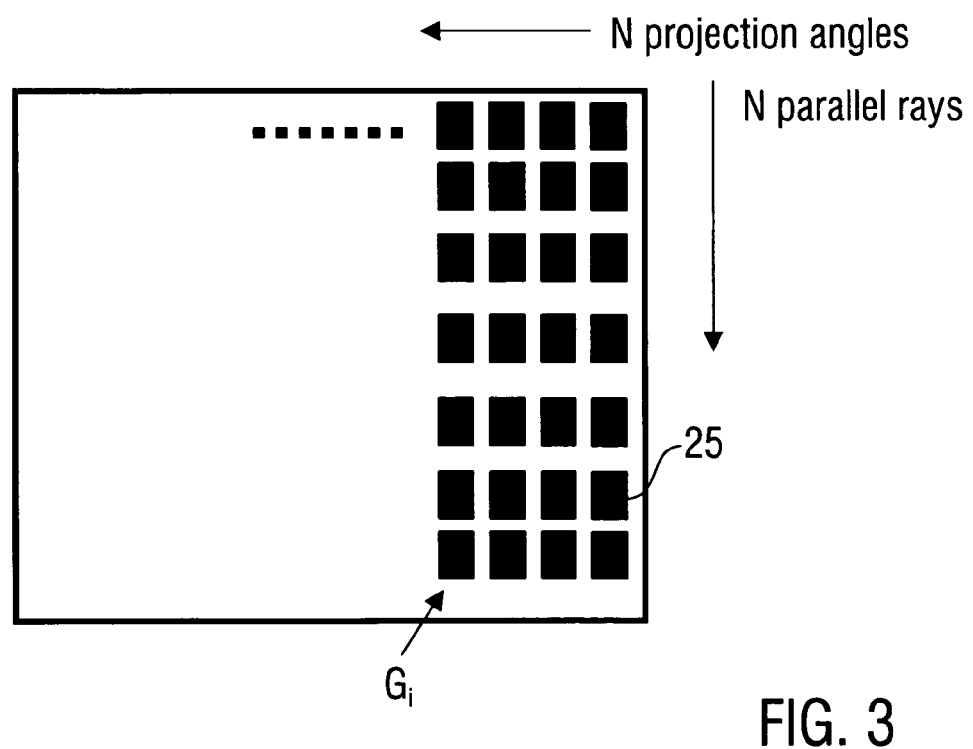
Figure 4:
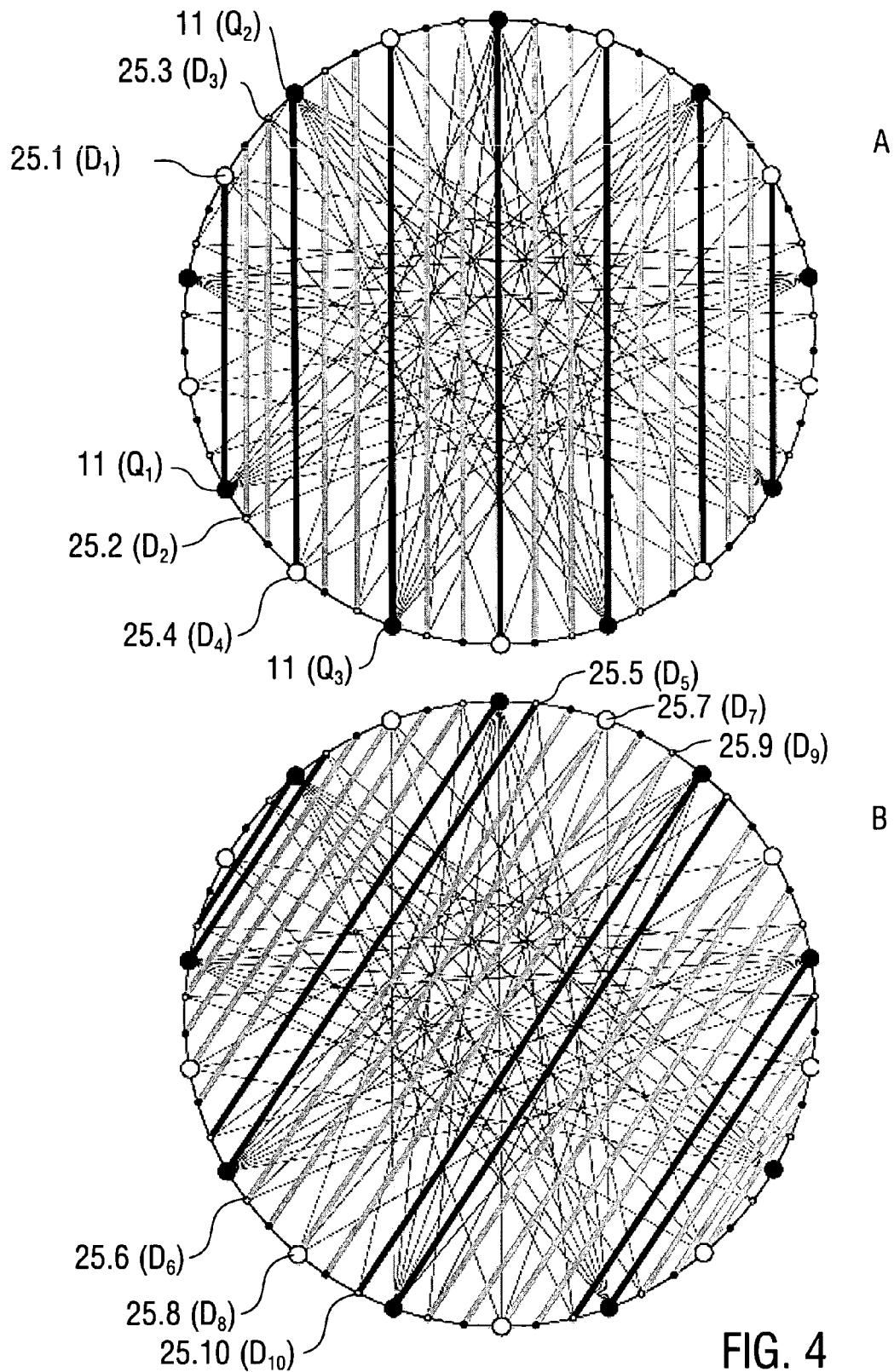
Figure 5:
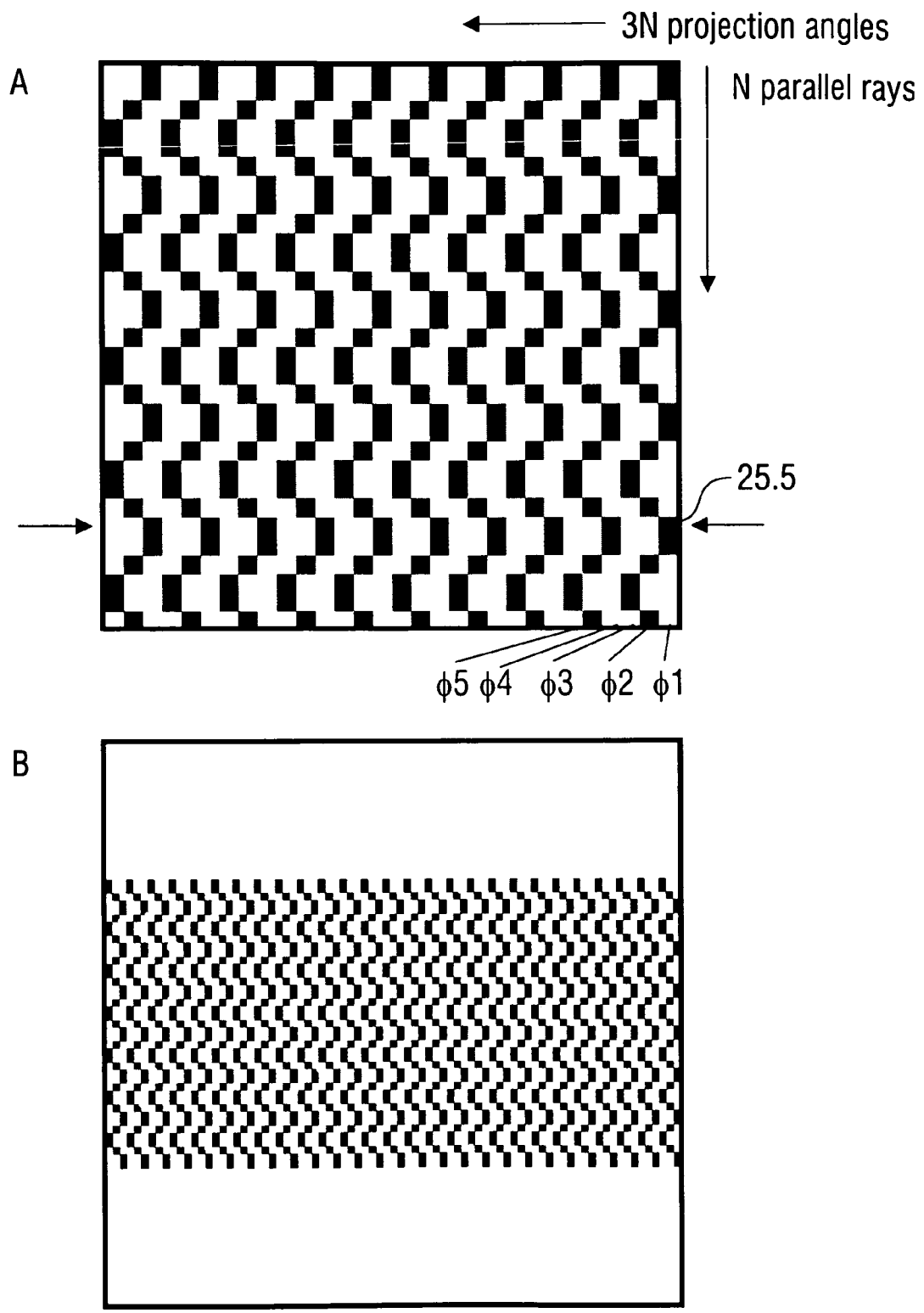
Figure 6:
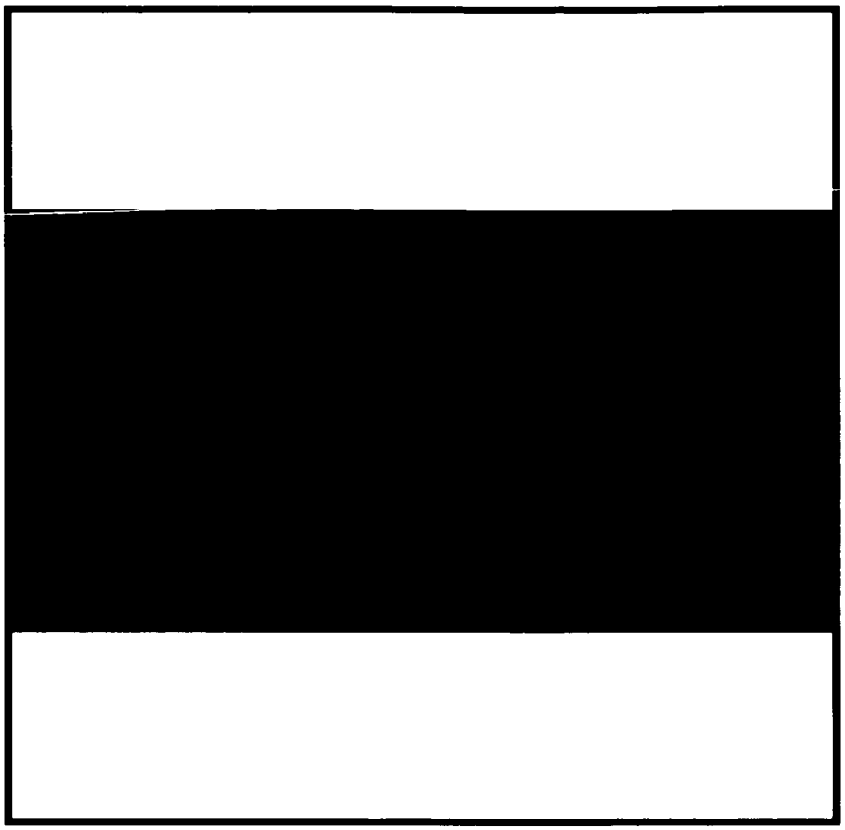

The step of constructing the projection profiles (step S3) is described with further details below. FIG. 2 schematically illustrates the irradiation of an object (ROI 2, inner disk) with a rotating fan beam. With the irradiation and detection conditions described in EP 04031043.5, complete Radon data will be obtained as shown in FIG. 3. For imaging ROI 2 with increased resolution, the detection conditions are changed (FIG. 4) resulting in incomplete measured Radon data (FIG. 5) which are subjected to the first interpolation according to the invention (FIG. 6).

In FIG. 2 (corresponding to EP 04031043.5), the assignment of the fan of X-ray beam components to groups of parallel X-ray beam components is schematically illustrated. The solid circles on the circumference of the outside circle (unit disk) in FIG. 2 denote the centre positions $Q_i$ of the X-ray source 11 from which fan beam components are emitted. Each of the positions $Q_i$ provides one view through the ROI 2. In practice, the number of views in a CT device is in the range of e.g. 500 to 1000. The empty circles denote centre positions $D_i$ of at least one detector element 25. With this arrangement (described in EP 04031043.5), the number of views is equal to the number of detector element positions. Only those lines having an intersection with the ROI 2 (the inner disk) are depicted. The positions $Q_i$, $D_i$ of the X-ray source 11 and the detector elements 25 have an equal angular spacing. With this geometry, the X-ray beam components that emit from the X-ray source 11 to the detector elements 25 automatically provide parallel lines.

As an example, the dashed lines $L_1$ represent a first set of parallel beams. The first line of $L_1$ (from below) corresponds to the first beam component of the fan beam emitted at the position $Q_1$ of X-ray source 11, while the third line of $L_1$ corresponds to the third beam component of the fan beam emitted at the changed position $Q_3$ of the X-ray source 11. Due to the odd number of the positions of X-ray source 11 and the detector elements 25, the second line of $L_1$ can be obtained from position $Q_2$ with the opposite irradiation direction. EP 04031043.5 is introduced into the present specification in particular with regard to further details of the resorting of non-parallel fan beam components of the fan beam in each position of the X-ray source 11 into groups of parallel fan beam components.

For a set of parallel lines obtained from assignment as shown in FIG. 2, the parallel dashed lines $L_1$ are located on the Chebyshev points $\cos[(2j+1)\pi/(2m+1)]$, $j=0, 1, \ldots, 2m$, on the axis that is perpendicular to the parallel direction and has a centre at the origin of the unit disk. EP 04031043.5 is introduced into the present specification in particular with regard to the description of further details of the Chebyshev points.

Projection values measured with the detector elements at different positions of the radiation source are arranged in discrete projection profiles such that all projection values being measured with the same projection direction contribute to the same projection profile.

In the left part of FIG. 2, a group $G_1$ of detector elements 25 is illustrated which provide projection values of one projection profile according to one particular projection direction. Each of the detector elements 25 is associated with one position in the projection profile (value position). As only projections having an intersection with the ROI 2 are measured, the projection profile includes seven value positions only. In practice, the projection profile includes e.g. about 50 to 1000 value positions. If the number of positions of the X-ray source 11 (number of views) equals the number of detectors 25 and each of the detectors 25 provides one attenuation value, the projection profiles are completely filled. This condition is fulfilled with the technique described in EP 04031043.5.

FIG. 3 shows a so-called sinogram representation of a plurality of groups $G_i$ of detector elements 25, each group $G_i$ relating to another one of N projection directions. This sinogram representation corresponds to the geometry described in EP 04031043.5. All detector elements 25 are hit from fan beam components at one of the positions of the X-ray source 11. Accordingly, all value positions of the projection profiles are occupied and the sinogram representation of FIG. 3 is completely filled.

FIGS. 4A and 4B illustrate amended detection conditions for imaging ROI with increased local resolution in accordance with the present invention. The unit disk is divided with equal angular spacing represented by small and large circles indicating theoretical and/or practical positions $Q_i$, $D_i$ of the X-ray source 11 and detector elements 25.1, 25.2, 25.3, ... of the detector device. As in FIG. 2, the X-ray beam components emitted from the X-ray source 11 to the detector elements 25 automatically provide parallel lines. The large circles being distributed with equal angular spacing denote the positions $Q_i$ of the X-ray source 11 from which fan beam components are emitted. The large and small circles denote all positions $D_i$ at which fan beam components can be detected with the detector elements 25.1, 25.2, 25.3, .... The number of views (large circles) is smaller than the number of detector element positions (all circles). In the illustrated example, the ratio of the number of detector element positions to the number of views is 3.

In practice, one single X-ray source 11 is rotated to the various circle positions. Due to the symmetry of irradiation and projection profile construction, fan beams are emitted at the solid large circles $Q_i$ only. Each of the positions $Q_i$ provides one view through the ROI. With this geometry, the number of views in a CT device can be selected in the range of e.g. 500 to 1000.

Each projection profile for constructing an image of the ROI comprises a plurality of parallel projections, which are obtained by an assignment (or resorting) of the beam components measured with the detector device. As the number of views is smaller than the number of detector element positions for practical reasons, resorting of non-parallel fan beam components of the fan beam in each position of the X-ray source 11 into groups of parallel fan beam components yields incomplete projection profiles as illustrated in FIGS. 4A and 4B.

For the particular projection direction indicated in FIG. 4A, parallel fan beam components can be detected with every third detector element only. As an example, with detector elements 25.1 and 25.4 at positions $D_1$ and $D_4$, parallel fan beam components can be detected, while with detector elements 25.2 and 25.3 at positions $D_2$ and $D_3$, fan beam components cannot be detected due to the lack of positions at which the X-ray source 11 emits fan beams.

If the projection direction is changed, the resorting scheme yields another distribution of the parallel fan beam components as indicated in FIG. 4B. The parallel fan beam components can be detected with two adjacent detector elements only separated by groups of four detector elements, where fan beam components cannot be detected. As a further example, with detector elements 25.5 and 25.10 at positions $D_5$ and $D_{10}$, parallel fan beam components can be detected, while with detector elements 25.6 to 25.9 at positions $D_6$ to $D_9$, fan beam components cannot be detected.

Generally, with N views and mN detector elements, only N parallel projection lines can be detected in average, while (m−1)N projection lines are not irradiated. As the result, the measured projection profiles with a number of mN value positions include (m−1)N empty value positions.

FIG. 5A shows a sinogram representation of a plurality of projection profiles, each corresponding to another one of mN possible projection directions $\phi 1$, $\phi 2$, $\phi 3$, $\phi 4$, $\phi 5$, .... Each vertical stripe represents one projection profile, which is formed by the detector elements detecting parallel fan beam components belonging to the same projection direction. The projection profile includes a plurality of value positions (pixels) corresponding to the detector elements contributing to the projection profile. The black and white pixels represent value positions corresponding to irradiated and non-irradiated detector elements, resp.

According to the above step S3, the projection profiles are constructed with the measured projection values. Contrary to FIG. 3, the sinogram representations of FIGS. 5A and 5B are not completely filled. As the occupation of value positions in the projection profiles is shifted with every new projection direction, the value positions delivering measured projection values and the empty value positions provide a predetermined pattern. With the example of FIGS. 4A and 4B, the projection profiles include empty positions with varying distributions depending on the projection direction. The projection profiles of the projection directions $\phi 2$ and $\phi 5$ correspond to FIG. 4A, while projection profiles of the projection directions $\phi 1$, $\phi 3$ and $\phi 4$ correspond to FIG. 4B.

For constructing the projection profiles, only fan beam components transmitted through the ROI are used. Fan beam components outside the ROI are not detected. Accordingly, the complete sinogram representation includes broad white regions as shown in FIG. 5B.

According to the above step S4, interpolation profiles are constructed on the basis of the projection profiles by filling the empty value positions (black pixels) by the first interpolation. To this end, measured projection values having the same value position in different projection profiles are considered. As an example, the group of projection values having the value position of detector element 25.5 is indicated with an arrow. The first interpolation is conducted within each group of measured projection values having the same value position in different projection profiles. Empty positions are filled with interpolation values and the sinogram representation is completed with pixels as shown in FIG. 6. As the result of the above step S4, the interpolation profiles are obtained including measured projection values and interpolation values.

Optionally, step S4 of calculating the interpolation profiles (FIG. 1) includes a further (second) interpolation for increasing the number of Chebyshev points within each interpolation profile. This embodiment of the invention has essential advantages for providing a zoom function of CT imaging. Within a group of the measured projection values and the first interpolation values of the respective interpolation profile, sub-value positions are calculated.

The second interpolation can be limited to a certain part of the ROI, like a particular organ within a part of the human body. In this case, only a portion of each interpolation profile can be subjected to the second interpolation.

According to the above step S5, the ROI or a part thereof is reconstructed with the OPED algorithm, which is applied to the interpolation profiles obtained in step S4. The description of the OPED algorithm image construction as described in EP 04031043.5 is introduced into the present specification by reference.

2. Recording of 3-dimensional Images

With the detection geometry of the invention, helical projection data can be processed for obtaining 3-dimensional images of the object. Accordingly, at least one of the object and the source-detector unit is translated in a predetermined direction, e.g. perpendicular to the projection directions during the step S2 of irradiating the object for obtaining the helical projection data. Preferably, the object under investigation, e.g. a patient, is shifted through the CT gantry, lying on a patient table, which is moving continuously. For collecting the helical projection data the detector device can be used as described above.

By this method a so-called helical or spiral CT data set can be gathered, including projection profiles with empty value positions, which are subjected to the first and optionally second interpolation as described above. In particular, the helical CT data set can be reconstructed in an analogue way as described above for obtaining a stack of 2-dimensional images which are combined to a 3-dimensional image of the object.

The invention claimed is:

1. Method of reconstructing an image function on the basis of a plurality of projection profiles corresponding to a number of projection directions through a region of investigation, wherein
   each projection profile being measured with a detector device having a plurality of detector elements and including a series of value positions the number of which being equal to the number of detector elements,
   measured projection values corresponding to projection lines parallel to the respective projection direction are assigned to associated value positions and
   the number of projection directions is smaller than the number of detector elements and a plurality of remaining value positions are empty,
the method comprising the steps of:
   assigning first interpolation values to the empty value positions for constructing a plurality of interpolation profiles on the basis of the projection profiles, wherein the first interpolation values are obtained from a first interpolation within a group of measured projection values having the same value position in different projection profiles, and
   determining the image function by applying a predetermined reconstruction algorithm on the interpolation profiles.

2. Reconstructing method according to claim 1, for each interpolation profile further comprising the step of:
   generating second interpolation values by a second interpolation within a group of the measured projection values and the first interpolation values of the respective interpolation profile.

3. Reconstructing method according to claim 1, wherein at least one of the first and second interpolation values are obtained from a spline interpolation.

4. Reconstructing method according to claim 3, wherein at least one of the first and second interpolation values are obtained from a spline interpolation with a spline function of order n with n≧3.

5. Reconstructing method according to claim 1, further comprising a step of:
   adjusting at least one interpolation parameter.

6. Reconstructing method according to claim 5, wherein the at least one interpolation parameter is adjusted in dependence on a predetermined geometric feature of the region of investigation.

7. Reconstructing method according to claim 1, wherein the step of constructing the interpolation profiles comprises a step of:
   resealing the interpolation profiles so that each interpolation profile covers a predetermined unit disk including the region of investigation.

8. Reconstructing method according to claim 7, wherein the application of the reconstruction algorithm comprises determining the image function by filtered back-projection or an iterative reconstruction method.

9. Reconstructing method according to claim 1, wherein the application of the reconstruction algorithm comprises determining the image function as a sum of polynomials multiplied with the measured projection values and the first interpolation values, wherein the polynomials are sums of orthogonal ridge polynomials.

10. Reconstructing method according to claim 1, wherein the image function is determined from Radon data measured in:
    an X-ray computer tomography (CT) device,
    an ultrasound tomography device,
    a PET imaging device,
    light tomography,
    a Gamma-ray imaging device,
    a SPECT imaging device, or
    a neutron based transmission detection system.

11. Imaging method for imaging a region of investigation in an object, comprising the steps of:
    directing at least one energy input beam at predetermined irradiation directions through the region of investigation,
    determining projection profiles corresponding to a plurality of predetermined projection directions through the region of investigation, wherein each projection profile includes measured projection values corresponding to a plurality of projection lines with the same projection direction, wherein the measured projection values comprise attenuation values measured with the plurality of energy input beams and each projection profile including a series of value positions, wherein measured projection values corresponding to the projection lines parallel to the respective projection direction are assigned to respective value positions and a plurality of remaining value positions are empty, and
    reconstructing an image function representing the region of investigation by subjecting the projection profiles to a reconstructing method according to claim 1.

12. Imaging method according to claim 11, wherein
    the at least one energy input beam comprises a set of fan beams each of which including a plurality of fan beam components, and
    each projection profile comprises attenuation values corresponding to fan beam components with parallel projection lines having the same projection direction but being contained in different sets of discrete fan beams.

13. Imaging method according to claim 11, wherein the irradiation directions are set subsequently by using a movable radiation source being rotated around the object.

14. Imaging method according to claim 11 further comprising the step of:
    representing an approximation of the image function as a visualized image to be obtained.

15. Imaging method according to claim 14, wherein the object comprises:
    a biological organism or a part thereof,
    a fluid composition,
    a solid material,
    a work-piece, and/or
    an object to be investigated for security reasons.

16. Computer program residing on a computer-readable medium, with a program code for carrying out the method according to claim 1.

17. Apparatus comprising a computer-readable storage medium containing program instructions for carrying out the method according to claim 1.

* * * * *